United States Patent
Magnin et al.

(10) Patent No.: US 7,773,206 B2
(45) Date of Patent: Aug. 10, 2010

(54) TANK FOR AN OPTICAL DEVICE FOR BLOOD ANALYSIS, ANALYSIS APPARATUS EQUIPPED WITH SUCH A TANK

(75) Inventors: Olivier Magnin, Montpellier (FR); Henri Champseix, Saint Gely du Fesc (FR); Serge Champseix, Tarnac (FR)

(73) Assignee: C2 Diagnostics, Montepellier Cedex (FR)

( * ) Notice: Subject to any disclaimer, the term of this patent is extended or adjusted under 35 U.S.C. 154(b) by 232 days.

(21) Appl. No.: 11/887,263

(22) PCT Filed: Mar. 22, 2007

(86) PCT No.: PCT/FR2006/000624
§ 371 (c)(1),
(2), (4) Date: Sep. 27, 2007

(87) PCT Pub. No.: WO2006/103336
PCT Pub. Date: Oct. 5, 2006

(65) Prior Publication Data
US 2009/0079962 A1    Mar. 26, 2009

(30) Foreign Application Priority Data
Mar. 31, 2005    (FR) .................................. 05 03117

(51) Int. Cl.
*G01N 33/48* (2006.01)
(52) U.S. Cl. ....................................................... 356/39
(58) Field of Classification Search .................... 356/39
See application file for complete search history.

(56) References Cited

U.S. PATENT DOCUMENTS

| 3,989,381 | A  |   | 11/1976 | Fulwyler |
| 4,673,289 | A  | * | 6/1987  | Gaucher ....................... 356/72 |
| 4,732,479 | A  |   | 3/1988  | Tanaka et al. |
| 4,786,165 | A  | * | 11/1988 | Yamamoto et al. ............ 356/23 |
| 4,997,275 | A  | * | 3/1991  | Gaucher et al. ............... 356/72 |
| 5,905,214 | A  | * | 5/1999  | Inami ......................... 73/865.5 |
| 6,228,652 | B1 | * | 5/2001  | Rodriguez et al. ............ 436/63 |
| 6,473,171 | B1 |   | 10/2002 | Buttry et al. |

* cited by examiner

Primary Examiner—Roy Punnoose
(74) Attorney, Agent, or Firm—Young & Thompson

(57) ABSTRACT

A flow-through tank 300 is suitable for an optical device 120 for the counting and/or differentiation of leucocytes in an automatic blood analysis apparatus 1. The tank has an analysis zone 304, in which the section of the tank has at least one transverse dimension between 1 and 5 millimeters. It can advantageously be produced, at least partially, from an injected plastic material.

19 Claims, 9 Drawing Sheets

Based on embodiment No. 4

Based on embodiment No. 4

Based on embodiment No. 4

Reference matrix Eosinofix without stabilization agent of the haemoglobin complex Eosinofix with DDAPS Eosinofix with Tiron Eosinofix with imidazole

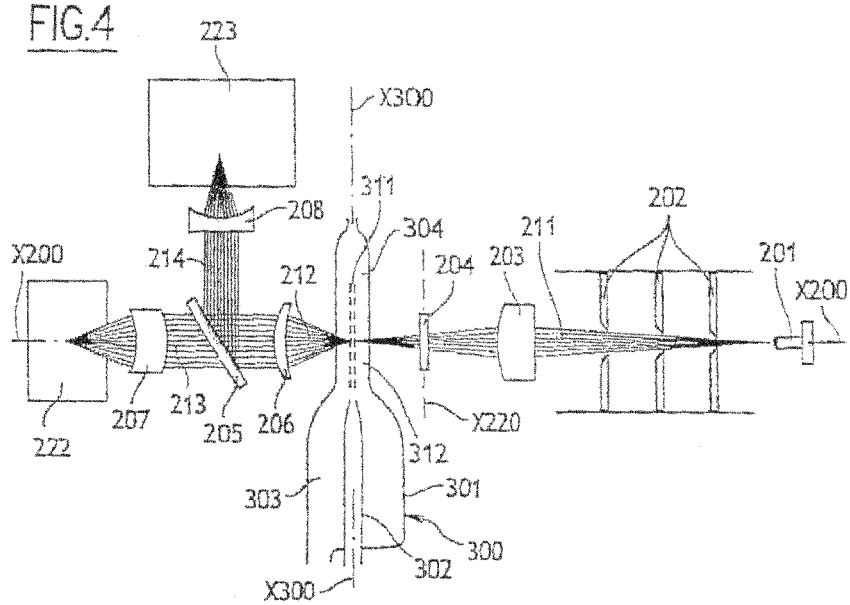
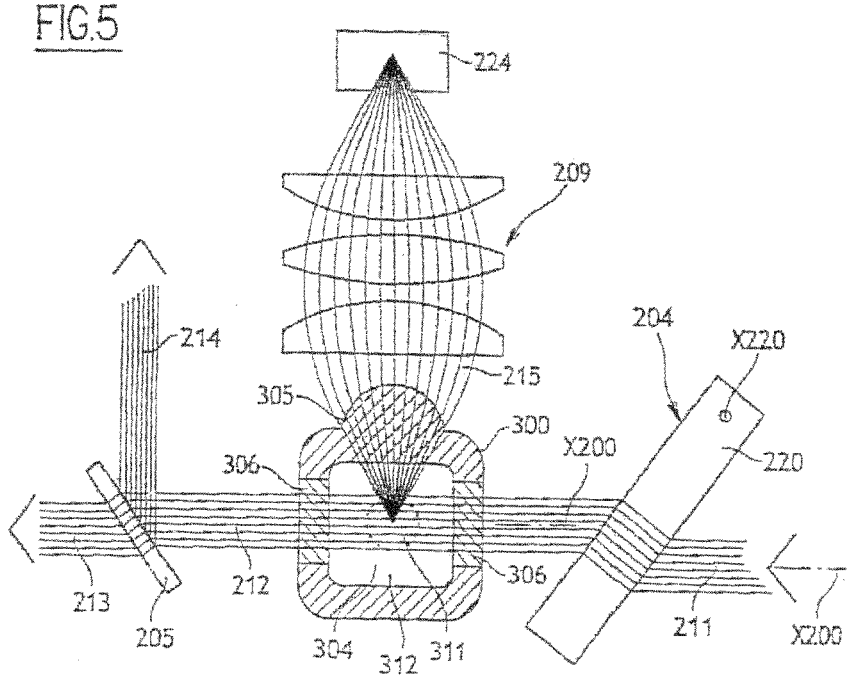

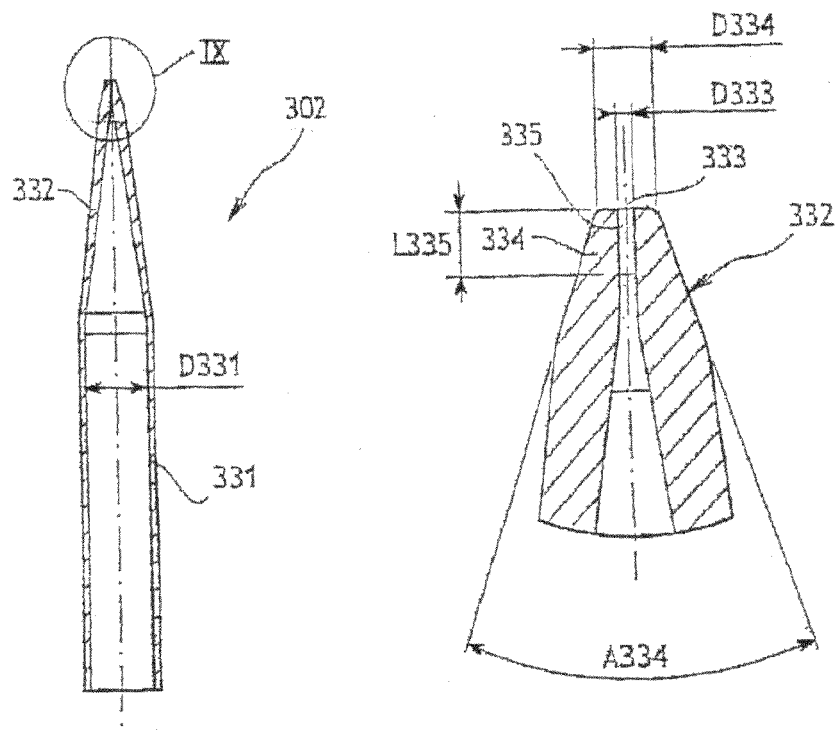
FIG.8
FIG.9
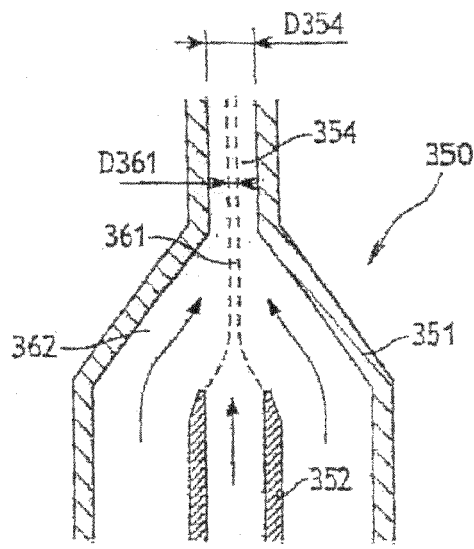
PRIOR ART
FIG.10

TANK FOR AN OPTICAL DEVICE FOR BLOOD ANALYSIS, ANALYSIS APPARATUS EQUIPPED WITH SUCH A TANK

The present invention relates to a flow-through tank for an optical device suitable for the counting and differentiation of leucocytes in an automatic blood analysis apparatus. It also relates to an analysis apparatus equipped with such a tank.

BACKGROUND OF THE INVENTION

Analysis of a blood sample generally seeks to determine:
the total number of leucocytes;
more specifically, the number of leucocytes by sub-populations (basophils, eosinophils, neutrophils, monocytes and lymphocytes);
the number of erythrocytes and platelets; and
the haemoglobin level.

Several analysis techniques are known, in particular:
assay of the haemoglobin is carried out after lysis of the erythrocytes, i.e. the destruction of the membrane of the cells of erythrocytes, and by measurement by spectrophotometry of the haemoglobin released in the medium; the assay of the haemoglobin also requires the stabilization of the haemoglobin in a complexed form (oxyhemoglobin or cyanmethemoglobin) in order to measure the absorbance of a single compound at the appropriate wave length.

total leucocyte count is carried out on the blood sample by resistivity with specific lysis of the erythrocytes and protection of the leukocytes.

differentiation of the leucocytes and the counting thereof by sub-population is carried out:
either by resistivity volumetric measurement after specific lysis of the erythrocytes, protection of the leucocytes and adjustment of the pH; this however does not allow differentiation of all the sub-populations in a single analysis;
or by optical way, in particular by flow cytometry; after specific lysis of the erythrocytes and protection of the leucocytes, by measuring different parameters (in particular diffraction, fluorescence, absorbance), on a flow of leucocytes in the axis of the narrow, medium and wide angles and optionally after addition of a labelling agent (for example chlorazol black, or a DNA or RNA labelling dye, or a fluorescent dye) and by measuring at different wave lengths; this technique allows differentiation of the sub-populations of leucocytes.

the erythrocyte and platelet count is carried out on a diluted sample without the addition of specific reagent by resistivity measurement.

Numerous automatic blood cell analyzers exist which use these techniques in order to obtain a blood sample analysis which is as complete as possible.

In these automatic apparatuses, two different analysis circuits traditionally coexist:
a first circuit designed to measure the haemoglobin and/or the total leucocyte count; and
a second circuit designed to carry out on the blood sample the differentiation and/or a leucocyte count by flow cytometry.

Each circuit is characterized by a dilution rate of the blood sample suited to the measurement means used, the addition of one or more reagents and appropriate means for implementation and measurement.

Thus, for the measurement of haemoglobin and the counting of the leucocytes, the circuit typically comprises a so-called counting tank in which the blood sample is diluted, a reagent in particular comprising the lysis compound of the erythrocytes, the stabilisation compound of the complex formed from the haemoglobin and the leucoprotective compound is added to it, and the following are measured directly in this cell: haemoglobin by spectrophotometry and the number of leucocytes by resistivity. The dilution rate is chosen so that the analysis solution is perfectly homogeneous and so that the detection apparatus is not saturated. This dilution rate is comprised between $1/100^{th}$ and $1/500^{th}$, generally between $1/160^{th}$ and $1/180^{th}$.

For leucocytic differentiation by flow cytometry, the circuit uses a tank for dilution of the blood sample to which one or more reagents containing an erythrocyte lysis agent, optionally a differentiation agent (for example a DNA or RNA leucocyte fluorescent dye) are added, then a fraction of this solution is taken in order to inject it into a flow-through optical tank of a flow cytometer. The dilution rate used here is less than $1/100^{th}$, allowing an optimal analysis time to be obtained with the cytometers currently available on the market (of the hydrofocus type).

Thus, conventionally at least two different reagents must usually be used for the two analysis circuits and two different dilutions of the blood sample are carried out in these two analysis circuits.

The main objectives of manufacturers are to simplify the existing automatic apparatuses by reducing the number of components and reagents, allowing reduction of the production and maintenance costs and the size of the automatic apparatuses, without however reducing the time of a complete blood sample analysis.

The present invention in particular aims to achieve these objectives.

Document WO 2004/003517 for this purpose proposes a method and equipment in which the two analysis circuits have means in common. The principle is to carry out a first dilution of the blood sample in a single dilution tank and to successively transfer fractions of selected volumes of this dilution to a measuring or counting unit, in order each time to measure or count different elements contained in the blood sample. In order to carry out a complete analysis, namely counting the erythrocytes and platelets, counting the leucocytes, measurement of the haemoglobin and leucocytic differentiation, the document describes the following solution: using a first transfer to count the erythrocytes and platelets, adding a lysis agent to the dilution tank, then carrying out a second transfer to count the leucocytes, carrying out a third transfer of lyzed dilution solution to measure the haemoglobin level, adding a leucocytic differentiation reagent, and carrying out a fourth transfer to realize the leucocytic differentiation in the measuring unit.

This principle may allow the use of a single so-called dilution tank, but it does not allow a saving of analysis time because the measurements or counting are carried out successively after each transfer of a fraction of the dilution. Moreover, it requires perfect control of the successive volumes of reagents and diluents transferred to the measuring unit. Moreover it also requires the use of several syringes and lysis reagents.

The objective of the present invention is also to overcome such drawbacks.

SUMMARY OF THE INVENTION

According to a first object, the present invention relates to a method for the automatic analysis of a blood sample as well as a mono-reagent and an apparatus for implementing this method.

The method according to the invention is characterized in that:
an analysis solution containing said blood sample, a diluent, and:
at least one compound to lyze the erythrocytes;
at least one compound to protect the leucocytes; and
at least one compound to stabilize the haemoglobin in the form of a chromogenic complex; is formed in a single dilution and analysis tank,
the haemoglobin level is measured in this analysis solution by spectrophotometry in said tank after the lysis of the erythrocytes; and
an appropriate quantity of this analysis solution is taken from said tank on which a leucocytic differentiation is carried out by an optical means.

The counting of the leucocytes can be carried out jointly in the analysis tank and/or with the optical means.

The counting of the erythrocytes and optionally of the platelets can be carried out for example in a previous stage of the method on a sample carried out in the single dilution and analysis tank.

Thus, the present invention is based on the concept of a single analysis solution used as is for the two types of analyses which were usually carried out in two separate circuits, namely on the one hand the measurement of the haemoglobin and optionally the counting of the leucocytes and, on the other hand, the leucocytic differentiation by optical means, said analysis solution combining the "reagent" compounds capable of carrying out at least these analyses by virtue of their nature and their quantity. The reagent compounds introduced are chosen to be chemically compatible with each other and in quantities suited to the targeted analyses. They can be chosen from the compounds typically used in the prior art. It is also possible to use a commercial formulation which is conventionally used to carry out a leucocytic differentiation, i.e. containing the compound for lyzing the erythrocytes and the leucoprotective compound, and to add to it the third reagent compound intended to stabilize the haemoglobin in the form of a chromogenic complex.

Due to this single analysis solution, the present invention in particular has the following advantages:
the automatic apparatus can comprise a single tank for preparation of the analysis solution,
the measurement of the haemoglobin can be carried out directly in this tank, and also the global counting of the leucocytes by resistivity measurement of the analysis solution;
it is possible to use a mono-reagent combining all the "reagent" compounds required for the measurement of the haemoglobin and for the leucocytic differentiation by optical means; this in particular allows simplification of the hydraulic circuits as will be seen below;
a mono-dilution of the blood sample can be carried out directly in the single dilution and analysis tank, with a dilution rate determined as a function of the measurement and detection means used. The mono-reagent can serve as a diluent for carrying out this mono-dilution. Preferably, a dilution rate will be chosen comprised between $1/100^{th}$ and $1/500^{th}$, corresponding to the dilution rate required for a measurement of the haemoglobin level, preferably also a rate of approximately $1/175^{th}$ ($1/173^{rd}$ in the embodiment given below).

With the possibility of using a mono-dilution and a mono-reagent, it is therefore possible, thanks to this first aspect of the invention, to greatly simplify the analysis equipment while still providing a complete analysis of the blood sample.

Means for optical measurement allowing an analysis of the leucocytes (counting and differentiation by sub-populations) at a dilution rate greater than $1/100^{th}$ are also proposed according to the invention and are defined and described below.

The present invention also proposes a lysis mono-reagent for the implementation of the method according to the invention, characterized in that it comprises:
at least one compound to lyze the erythrocytes;
at least one compound to protect the leucocytes; and
at least one compound to stabilize the haemoglobin in the form of a chromogenic complex.

Such a mono-reagent allows measurement by spectrophotometry of the hemoglobin concentration of a blood sample and a leucocytic differentiation by optical means. It also allows the resistive and/or optical counting of the leucocytes. Preferably it is chosen so as to allow the differentiation of at least 5 sub-populations. Preferably it is chosen so that it does not contain cyanides.

According to the invention, the compound to lyze the erythrocytes is preferably constituted by at least one cationic surfactant. In a preferential manner which is known per se it is chosen to form an oxyhemoglobin complex (as it is non-toxic compared to a cyanmethemoglobin complex which involves cyanide ions). The cationic surfactant is therefore also chosen such that it oxidizes the released haemoglobin so as to form only an oxyhemoglobin complex. The quantity of cationic surfactant is therefore chosen so as to efficiently haemolyse the erythrocytes and oxidize the haemoglobin released. It is preferably chosen from:
the quaternary ammonium salts, preferably alkyltrimethylammonium salts and still more particularly cetyl-, dodecyl-, tetradecyl- and hexadecyltrimethylammonium bromides and chlorides;
pyridinium salts;
long-chain ethoxylated amines; and
alkyl sulphates (SDS).

The leucoprotective compound according to the invention is a compound which delays or prevents the destruction of the leucocytes. Preferably it is a non-ionic or amphoteric surfactant preferably chosen from:
ethoxylated alcohols, in particular 2-phenoxyethanol, polyoxyethylenealkylphenylethers, such as the commercial products IPEGAL990®, TERGITOL NP9®, TRITON® X100 or X114, Plurafac® A38 or Brij35®);
betaines and sulphobetaines of quaternary ammoniums in particular lauramidopropyl betaine (LAB), and dodecyldimethyl-3-ammonio-1-propanesulphonate (DDAPS) or tetradecyldimethyl-3-ammonio-1-propanesulphonate (TDAPS);
tertiary amine oxides, such as N,N-dimethyllaurylamine-N-oxide (LDAO) or 3-[(cholamidopropyl)-dimethylamino-]-1-propane sulphonate (CHAPS or CHAPSO);
the glycosidic type compounds and more particularly a triterpene saponin;
the glucidic type compounds (mannitol, D-glucose, trehalose, dextran sulphate).

The compound which stabilizes the haemoglobin in the form of a chromogenic complex is preferably chosen from:
mono or polydentate chelates presenting ligand atoms (non-binding pairs: O, N, S, and carboxy COO— groups etc.) in particular:
ethylene diamine tetraacetic acid (EDTA) or ethylene glycol-bis-(3-aminoethylether)N—N'-tetraacetic acid (EGTA) and in particular their sodium or dipotassium salts;
potassium oxalate $K_2O_xO_x=C_2O_4^{2-}$;
hydroxylamine salts (preferably hydrochlorites); and organic acids (in particular formic or acetic).

the aromatic compounds (mono or polydentate chelates) comprising ligand atoms (having non-binding pairs: 0, N, S etc.), in particular:
Tiron®
8-hydroxyquinoline and its derivatives;
pyridine or bipyridine and their derivatives;
1,10-phenanthroline and its derivatives;
the phenolic compounds (mono or bis and their derivatives);
pyrazole and/or the pyrazolones and their derivatives;
imidazole and its derivatives
sulphosalicylic acid; and
saponins, tertiary amine oxides, betaines and sulphobetaines of quaternary ammoniums (such as DDAPS, TDAPS, LAB).

In addition to the three compounds defined according to the invention, it is possible to add to the (mono)-reagent(s):

at least one dye (or mixture) specifically labelling certain leucocytes and more particularly eosinophils (or basophils), in order to allow the distinguishing of at least the 5 main leucocyte sub-populations, chosen from:
cyanines;
Oxazine 750;
Wright and Romanowsky reagents;
DAPI;
Clorazole black E;
Toluidine blue;
Astra Blue;
thiazole orange G. or blue;
other fluorescent reagents.

at least one fixing agent allowing stiffening of the membrane of the leucocytes which is preferably an aldehyde and more particularly glutaraldehyde or formaldehyde;

at least one wetting agent in order to optimize the fluidics and prevent the formation of bubbles which also act as solubilizers of the debris, chosen from:
alcohols (methanol ethanol or propan-2-ol);
glycols (ethylene or propylene glycol);
ethoxylated glycols (particularly Triton X100® or Brij35®);
glycosidic compounds TWEEN80® or TWEEN20®;

the concentration of the fixing agent and of the solubilizer being strictly limited, as an excess can prevent the lysis of the erythrocytes and modify the optical properties of the leucocytes; and a buffer system for setting the pH between 5.0 and 10.0 and preferably between 6.0 and 8.0 and optimally close to neutrality (7.0±0.4). The choice of such a pH aims to respect the native conditions of the cells. Moreover this pH allows a better dissolution of the constituents used according to the invention. Said buffer is constituted by a pair of salts (inorganic or organic) adjusted to the above-mentioned pH by hydrochloric acid or soda (4-6N), chosen from:
sodium or potassium dihydrogen phosphate/hydrogen phosphate $H_2PO_4^-/HPO_4^{2-}$;
sodium hydrogen carbonate/carbonate $NaHCO_3/Na_2CO_3$
a citric acid/sodium citrate (III) buffer
TRIS-HCl
triethanolamine (TEA)
imidazole
an acid chosen from:
the organic acids: phthalic, sulphosalicylic or formic, which also contribute to the formation and stabilization of the chromogenic complex of the haemoglobin); and
the mineral acids: HCl, $H_3PO_4$ etc.

a background salt ensuring a conductivity of the order of 10 to 50 ms/cm required for the resistivity measurement and an osmolarity of the order of 120 to 500 mOsm and preferably close to isotonicity (290±5 mOsm), chosen from:
sodium chloride NaCl;
potassium chloride KCl;
magnesium chloride $MgCl_2$;
calcium chloride $CaCl_2$;
anhydrous sodium sulphate $Na_2SO_4$;
this background salt being able to be comprised in the buffer system;

at least one preservative, having antioxidant, and/or antibiotic properties chosen from:
2-phenoxyethanol;
parabens;
BHT;
isothiazolones (Proclin® 150 or 300);
imidazole or urea derivatives;
antibiotics;
a natural antibiotic cellular penetration compound (ionophore) which also facilitates the penetration of the dye or dyes chosen from:
ionophore I for $NH_4^+$ (nonatine);
ionophore III for $Ca^{2+}$ (calcimycine);
ionophore for $Cl^-$;
ionophore I for $K^+$ (valinomycine).

The constituents according to the invention are summarized in the table below as well as ranges of appropriate concentrations.

| Constituent | Quantity |
| --- | --- |
| Cationic surfactant (lysis agent) | 0.1-50 g/L |
| Leucoprotective surfactant | 0.1-20 g/L |
| Chelate of the haemoglobin complex | 0.0001-10 g/L |
| Dye | 0.01-1 g/L |
| Fixing agent | 0.01-2% w/v |
| Wetting agent | 0-50% v/v |
| Buffer | 0-6 g/L |
| Background salt | 1-50 g/L |
| Acid | Appropriate quantity to adjust the pH |
| Preservative | Appropriate quantity 0.1-3 g/L |
| Ionophore | Effective quantity 0-200 mg//L |
| Distilled water qsf | Qsf 1 L |

The present invention also proposes an apparatus for implementing the method according to the invention which is characterized by:
an analysis tank which is able to receive said analysis solution;
a means for measuring the level of hemoglobin present in said analysis solution by spectrophotometry in said tank;
a means for sampling said analysis solution;
a means for optical measurement on said sample in order to produce a leucocyte analysis.

According to a second object, the present invention relates to an optical device for an automatic apparatus for the automatic analysis of a blood sample, particularly advantageously also for the implementation of the method according to the first object of the invention.

As mentioned above, certain sub-populations of leucocytes can only be differentiated by optical measurements, for example a measurement of the diffraction by the cell at one or more angles, or a measurement of the absorbance of the cell. The optical systems for characterization of a blood cell have a common base in which a light source is located emitting a light beam, an optical tank in which the blood cells cross the light beam, a system for adjustment of the light beam to the flow of cells and means for measuring the light originating from the optical tank after interception by the cells. In particular in the case of leucocyte characterization, the leucocytes move in a flow in the tank. They are illuminated therein by a light beam focussed on the flow, which is called the sample flow.

Such devices are costly: in particular, the lasers used as light sources, which are also bulky and generally require a thermal dissipation system; the laser diodes, like the lasers, require costly alignment systems. The light beams emitted by these sources have a transverse distribution of light which is approximately Gaussian in shape. Thus, the intensity is only approximately constant and maximal in a narrow and central part of the ray. The alignment systems allow this central part to be aligned with the sample flow. Moreover, the width of the sample flow must not exceed that of this central part, and the closer these two widths are, the greater the precision of the alignment system must be. As a result, it is necessary to reduce the width of the sample flow as much as possible.

The sample flow containing the blood cells to be counted and/or to be differentiated must be narrower the more the light is focussed. Thus, a flow is used in which the width of the section is less than 50 μm, which must cross the light beam which is itself focussed into a narrow beam with a larger section than that of the sample flow. This requires a particularly precise and therefore costly system for injection of the flow into the optical tank. In the prior art, such a result is obtained using a hydrofocus type system (abbreviation of the English expression "hydrodynamic focusing"). The sample flow is surrounded with a sleeving flow. An injector for the sample flow is immersed in the centre of the sleeving flow. The sample flow thus created is widened or focussed as it travels from the injector to the zone illuminated by the light beam, so that it has, at this point, a desired width of approximately 5 to 50 μm in diameter. A single or a double sleeving is sometimes necessary in order to achieve this objective.

Moreover, as mentioned previously, given the level of precision required, an adjustment system is essential in order for the flow of cells to be coincident with the light beam. Two approaches are possible: the flow of cells or the light beam can be moved. If it is chosen to move the flow of blood cells, all of the optical tank unit must be moved. When this option is adopted, the tank is mounted on a translation table which ensures a precise and uniform movement along two axes due to its ball bearings. Such a precision mechanical assembly is quite costly. It is also possible to move the light beam in order to make it coincident with the flow of blood cells. This is generally achieved using several adjustable prisms. This solution, which combines optical elements with precision mechanics also involves high costs.

Moreover, when it crosses the light beam, the blood cell deflects the trajectory of the light rays. The intensity and the angle of the deflected rays allow information on the cell type to be obtained. Two ranges of angles are generally used: narrow angles less than ten degrees with respect to the optical axis and wide angles approximately perpendicular to the optical axis. In the range of the narrow angles, two items of information are useful: the losses in the axis and the diffraction. Perpendicular to the optical axis, the diffusion and the fluorescence are generally measured. For the two ranges of angles, the light must therefore be distributed into two different channels. This is generally achieved with dichroic mirrors or with interference filters. The optical components are both produced by depositing thin films on a glass substrate. They have good efficiency but a great disparity exists between one filter and another and their lifetime is limited. They must therefore be regularly replaced.

All these generally bulky devices are also fragile and require maintenance, which is also very costly. Such devices are therefore restricted to analytical laboratories which are large enough to be able to invest in such automatic apparatuses.

The purpose of the invention is to propose a device for leucocyte differentiation and/or leucocyte counting which is simpler and more economical both to produce and to maintain, allowing the use of automatic apparatuses, equipped with the device, by smaller laboratories, while retaining adequate quality of measurement.

According to the second object of the invention, an optical device for counting and/or the differentiation of leucocytes in an automatic blood analyzer is proposed, characterized in that it comprises a light source of the electroluminescent diode type in order to illuminate a blood sample circulating in the optical tank according to an injection axis, using a source light beam. Such a diode allows a light beam to be obtained which is more homogeneous over the width of its section and therefore of a larger and more homogeneous reading zone.

Preferably, the diode emits light the wave length of which is less than 600 nanometers, and still more preferably less than 500 nanometers. Such a wavelength allows a better diffraction efficiency, therefore better precision for measurements using diffraction.

Moreover, the width of the beam emitted by the optical device, i.e. the source beam which illuminates the sample flow, is advantageously comprised between 50 and 200 microns (μm), close to the injection axis, which allows illumination of a wider sample flow, while allowing adequate precision in the measurements carried out. Yet more advantageously, this width is comprised between 90 and 120 microns. Such a flow width is in particular permitted by the use of electroluminescent diodes.

Preferably, the source light beam is emitted approximately in the direction of the tank, approximately transversely to the direction of flow of the sample. A transparent slide designed so that the source beam passes through it between two opposing surfaces, which is rotatably mounted and arranged between the diode and the tank can allow the light beam to be moved in a transverse direction, thanks to its double refraction when it passes through the slide. The rotation of the slide allows modification of the angle of incidence of the beam on the slide, and thus adjustment of the value of the transverse shift. Preferably, the transparent slide is rotatably mounted about an axis which is approximately parallel to the movement of the blood sample in the tank.

Beyond the optical tank, means for separation by Fresnel losses are advantageously used for an incident resulting light beam originating from the source light beam, thus separating said beam into an axially-resulting beam and at least one beam resulting from loss constituted by Fresnel losses whilst passing through the separation means. The separation means comprise at least one separation surface which is a surface in a transparent separation material, the axial beam having passed through the transparent material and the beam originating from the Fresnel losses having been reflected by the separation surface, said surface being slanted in relation to the light beam beyond the tank. A single inexpensive glass slide can serve as separation means. Moreover it has a virtually unlimited and maintenance-free lifetime, unlike dichroic mirrors or interference filters.

The device can also comprise an apparatus for measuring the light of the axially-resulting beam and at least one other apparatus for measuring the light of at least one beam originating from the Fresnel losses. These measuring apparatuses can in particular comprise means for measurement of either the fluorescence, the light losses close to the axis or the diffraction close to the axis. It can also comprise means for measuring the diffraction of the light beam at wide angles by the sample in the tank. By way of example, these wide angles can be angles comprised between 60° and 150°.

The device can also comprise, in the path of the beam in front of the tank, at least one diaphragm blocking spurious light.

The invention also relates to a haematology apparatus, in particular an automatic blood analyzer equipped with such a device.

According to a third object, the present invention also relates to a flow-through optical tank for an optical device suitable for the counting and differentiation of leucocytes, for example a flow cytometer, as well as an analysis apparatus equipped with such a tank. The aim of the invention is to propose a tank which is simpler and more economical both to produce and to maintain, allowing the use of automatic apparatuses equipped with this tank by smaller laboratories, while retaining an adequate quality of measurement.

According to the invention, a flow-through tank for an optical device for the counting and differentiation of leucocytes in an automatic blood analyzer, is characterized in that in an analysis zone of the tank, the section of the tank has at least one transverse dimension comprised between 1 and 5 millimetres. This section can be approximately rectangular and the transverse direction can be measured on one and/or the other of the sides of the rectangle.

Such a tank can thus be produced, at least partially, from an injected plastic material. Such a tank is produced in a particularly advantageous manner compared to the tanks of the prior art, generally formed of quartz walls assembled by bonding.

The tank can also comprise at least one lens moulded in one piece with the tank. This at least one lens can comprise a lens envisaged to be arranged laterally in relation to an optical axis. It can comprise a hemispherical lens.

The tank can comprise along an optical axis, a window for the introduction of a light beam and a window for the beam to exit. At least one window can be moulded in one piece with the tank and/or be an insert in a transparent material, for example quartz or glass.

The tank can advantageously comprise an injector for a sample flow and means for forming a sleeving flow around the injection flow. The injector can comprise an outlet orifice the diameter of which is comprised between 20 microns and 150 microns, allowing a sample flow to be obtained which is noticeably larger than the flows of the prior art. By contrast to the devices of the prior art, it is not the sleeving flow which dictates the width of the sample flow by stretching it, but the shape and the section of the injector outlet. The sleeving flow therefore does not play an active role, but merely a passive role, in particular, for example for centering of the sample flow in a wide tank.

According to a first embodiment, this injector can be formed in one piece in a more or less rigid material. This material can be, for example, a stainless steel, a ceramic, synthetic ruby or a plastic material or several of these materials.

According to a second embodiment this injector can comprise a rigid structural tube, for example made of metal, for example made of stainless steel, and inside the structural tube, a plastic sheathing tube ending in a nozzle formed in one piece with the sheathing tube. The plastic material of the injector can be a polytetrafluoroethylene, which allows the sample to circulate more easily in the tube and reduces the risk of fouling up.

The invention also relates to an injector for a tank according to the invention, which injector is produced according to one of these embodiments.

The invention also relates to a haematology apparatus, in particular an automatic blood analyzer, equipped with a tank according to the invention.

According to a fourth object, the present invention also relates to a hydraulic device for a haematological analysis apparatus, which is simpler and more economical both to produce and to maintain and which allows the use of automatic apparatuses, equipped with such a device, by smaller laboratories, while retaining an adequate quality of measurement. The present invention also relates to an analysis method suited to such a device.

The present invention thus proposes a hydraulic device for a blood analysis apparatus, in particular an automatic apparatus, comprising means for injecting under pressure a sample flow into a flow-through optical tank and for creating a liquid sleeving flow around the sample flow, with a sleeving liquid, characterized in that it comprises means for adjusting a flow rate of the sample flow with respect to the flow rate of the sleeving liquid. Such adjustment can make it possible to maintain homogeneous and approximately non-turbulent flows in the tank.

The injection means can comprise syringes, a hydraulic circuit and solenoid valves. These means can comprise means for injecting the sample under pressure relative to the sleeving flow.

This device can advantageously comprise means for forming a piston for the sample injected with a displacement liquid. Such a displacement liquid makes it possible to use only a small sample sufficient for the analysis, the rest of the liquid required for the injection being a liquid available in the analysis apparatus, and not as precious as the sample.

The sleeving is particularly useful when using a tank with a wide section while maintaining a small section for the sample flow. As one of the means for adjusting the sample flow in relation to the sleeving flow, the device can advantageously comprise means for adjusting a flow rate of the displacement liquid with respect to the flow rate of sleeving liquid. The adjustment means can comprise means for a pressure drop in a branch circuit for the displacement liquid and/or means for a pressure drop in a branch circuit for the sleeving liquid. For example, the pressure drop means can be chosen from a known length of a calibrated tube, a fixed hydraulic resistance and a variable resistance.

The hydraulic device can comprise only one motorization, for example a single electric motor, in order to generate the sample flow and the sleeving flow simultaneously. Moreover, it can comprise at least two syringes in order to generate the sample flow and the sleeving flow, the syringe pistons being firmly attached to each other. They thus have a common movement and the sample and sleeving flows are indeed simultaneous.

In particular, a hydrofocus tank from the prior art can be used with a circuit such as described previously according to the invention, the injection of the sample into this tank can take place without pressure relative to the sleeving flow.

According to the invention, a method for the analysis of a blood sample in a flow-through cytometer is also proposed, characterized in that a blood sample is injected, optionally under pressure, into a flow-through tank of the cytometer, the sample forming a sample flow there and a liquid sleeving flow is created around the sample flow, with a sleeving liquid, characterized in that the flow rate of the sample flow is adjusted with respect to the flow rate of the sleeving liquid.

In particular, it is possible to introduce the sample into an injection branch of a hydraulic circuit, and to introduce upstream of the sample in the injection branch, a displacement liquid, the displacement liquid serving to push the sample during its injection into the tank. This displacement liquid can be chosen from a reagent and a diluent, preferably a reagent. There is therefore no point in providing a liquid other than that which is strictly necessary for the preparation of the sample with a view to its analysis or analyses.

It is also possible to create around the sample flow in the tank, a sleeving flow with a sleeving liquid. This sleeving liquid can also be chosen from a reagent and a diluent, preferably a diluent. In this case also, there is not point in providing a liquid other than those which are strictly necessary for the preparation of the sample with a view to its analysis or analyses.

In the case where a hydrofocus method, or a tank according to the third object of the invention, is used, it is advantageous to adjust the flow rate of displacement liquid with respect to the flow rate of the sleeving liquid, for example by introducing a pressure drop in a branch circuit for a displacement liquid and/or pressure drop means in a branch circuit for a sleeving liquid.

In a method according to the invention, in particular for a tank according to the third object of the invention, it can easily be provided that the blood sample has a dilution rate of at least $1/100^{th}$. In fact, in such a method, the sample can be introduced under pressure relative to the sleeving liquid, into the tank, at a velocity greater than that of the methods of the prior art, and with greater section widths for the sample flow in the tank. Thus, without increasing the analysis time, for a differentiation and a counting of the leucocytes, a dilution rate can be used which is identical to that used conventionally for the measurement of haemoglobin, in particular dilution rates comprised between $1/100^{th}$ and $1/500^{th}$, particularly between $1/160^{th}$ and $1/180^{th}$.

The invention also relates to a haematology apparatus, in particular an automatic blood analysis apparatus, characterized in that it comprises a hydraulic device according to the invention.

BRIEF DESCRIPTION OF THE DRAWINGS

The present invention will be better understood and other advantages will become apparent in light of the following description of embodiments, which description is made in particular with reference to the attached drawings in which:

FIG. 4 is a diagrammatic longitudinal view of an optical device unit according to the second object of the invention;

FIG. 5 is a more detailed diagrammatic longitudinal view of the optical device of FIG. 4, in a plane perpendicular to that of FIG. 4;

FIG. 8 is a longitudinal section view of a second embodiment of an injector for an optical tank according to the invention;

FIG. 9 is a longitudinal section view of one end of the injector of FIG. 8;

FIG. 10 is a longitudinal section view of a tank illustrating a method of the prior art for injecting the blood sample into the tank.

DETAILED DESCRIPTION OF THE PREFERRED EMBODIMENTS

Figure 1:
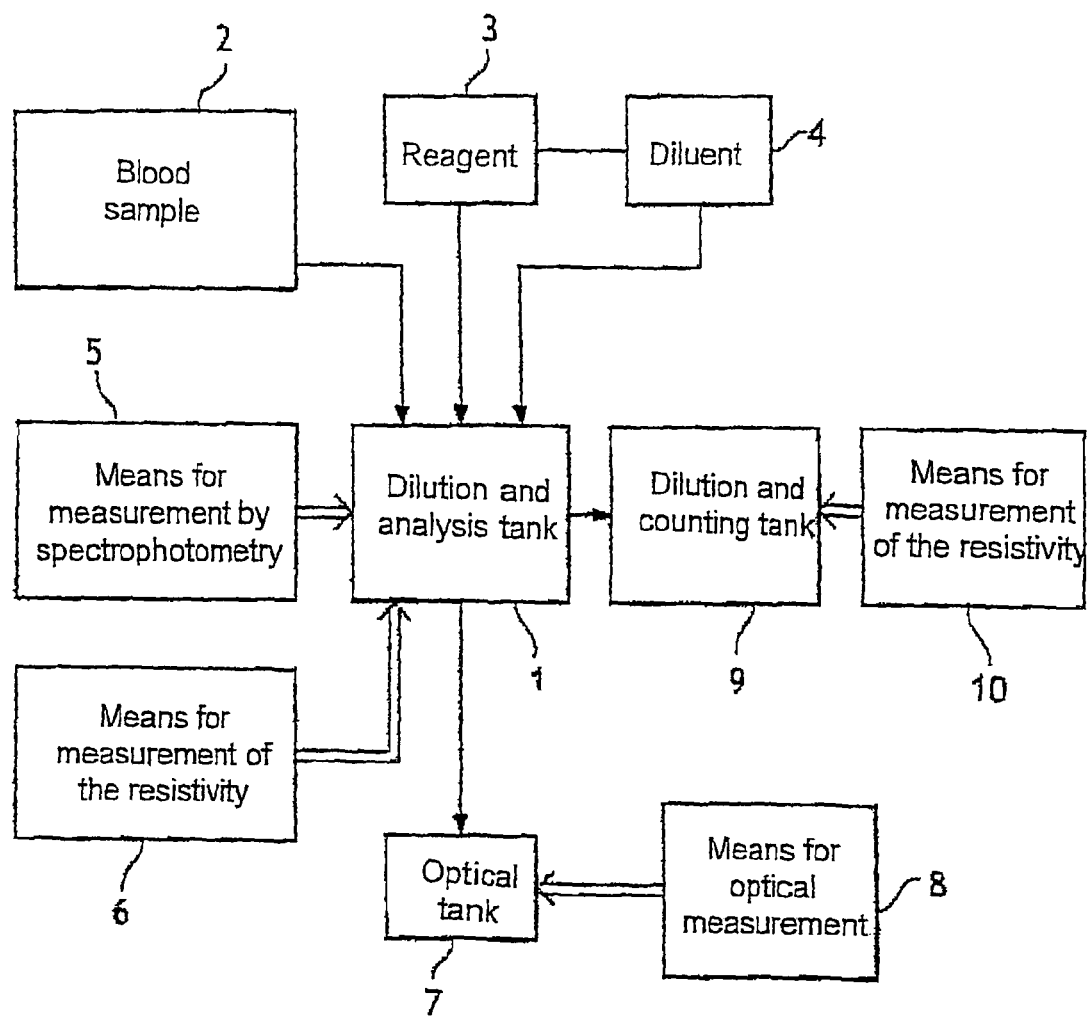
FIG. 1 diagrammatically illustrates an example of equipment according to the first object of the invention.

FIG. 1 diagrammatically illustrates a single dilution and analysis tank 1 which can be supplied with a blood sample 2 to be analyzed, a diluent 3 and a reagent 4 together forming an analysis solution. This tank 1 is equipped with means for measuring by photometry 5 the haemoglobin level in said analysis solution and means for measuring 6 the resistivity of said analysis solution in order to count the total number of leucocytes. Means are generally provided for taking a fraction of the analysis solution from the analysis tank 1 and for injecting it into an optical tank 7 equipped with optical measurement means 8 (for example a flow cytometer) for an analysis of the leucocytes. According to the example chosen, means are also provided for taking a fraction of a pre-solution constituted by the sample of blood and diluent, and introducing it into a counting and dilution tank 9 equipped with means for measuring the resistivity 10 of said fraction in order to count the erythrocytes and platelets. The equipment is conventionally equipped with heating means in order to obtain a thermostatically-controlled temperature of approximately 35° C. This temperature allows optimal lysis reaction time and quality of the erythrocytes.

The equipment operates in the following manner:

one aliquot of blood (15.6 µl) is injected into the analysis tank 1 and diluted with 2 ml of diluent so as to form an analysis pre-solution; the dilution rate is $1/130^{th}$;

a very small fraction (approximately 20 µl) is taken from this analysis pre-solution and deposited in the tank 9 for counting the erythrocytes and platelets;

0.7 ml of reagent is then added to the remaining pre-solution in the analysis tank 1: the lysis lasts for approximately 10 seconds (in order to destroy the erythrocytes, form and stabilize the oxyhemoglobin complex), the analysis solution thus formed has a final dilution rate of approximately $1/173^{rd}$; a fraction of said analysis solution is taken and injected into the optical tank 7 where the analysis of the leucocytes can take place (counting and/or differentiation of the leucocytes by sub-populations); simultaneously in the analysis tank 1, the leucocytes are counted by a resistivity measurement and the haemoglobin by a measurement by absorbance at the wave length of the oxyhemoglobin complex formed.

An optical device according to the invention, particularly suitable for a leucocytic analysis of an analysis solution having a dilution rate lower than $1/100^{th}$ is described below, more particularly suitable for a dilution comprised between $1/160^{th}$ and $1/180^{th}$. Conventionally, a dilution rate of $1/160^{th}$ is considered to be lower than a rate of $1/100^{th}$.

Of course variant embodiments of the method and of the equipment described above are possible:

for the equipment: means can be provided for separately introducing the lysis compound, the leucoprotective compound and the compound stabilizing the complex formed with the haemoglobin in the analysis tank 1, and therefore rather more in the form of a mono-reagent; the means 6 for measuring the resistivity of the analysis solution are optional; the total number of leucocytes being able to be obtained by optical analysis of the analysis solution; similarly the counting tank 9 and the means for measuring 10 the resistivity in this tank can be provided only if a complete analysis of the blood sample is desired;

likewise for the method: the introduction of the reaction compounds can be envisaged independently or collectively in place of a mono-reagent, the introduction being able to be carried out simultaneously or successively; the previous stage of counting the erythrocytes and platelets and the stage of global counting of the leucocytes can be omitted; moreover, two successive dilutions of the blood sample can be carried out: a first dilution which is particularly suitable for a leucocyte differentiation (approximately to $1/80^{th}$) as takes place in the known standard hydrofocus-type cytometer, from which the fraction required for this leucocyte differentiation is taken, then at a second moment in time a second dilution suitable for measurement of the haemoglobin (comprised between $1/100^{th}$ and $1/500^{th}$) as is possible with the known spectrometers.

According to yet another variant, the tank 1 can serve at a second moment in time to carrying out counting the erythrocytes and platelets after cleaning, by filling the tank with a sample waiting in a syringe needle.

The results obtained will now be described with a specific example of (mono)-reagent according to the invention:

A mono-reagent is prepared using the Eosinofix® formulation from the company ABX marketed for leucocyte determination in flow cytometry and containing for this purpose a compound for lyzing the erythrocytes and a leucoprotective compound (cf. patent EP0430750 by ABX). According to the invention, a compound stabilizing the haemoglobin complex was added.

Figure 2A:
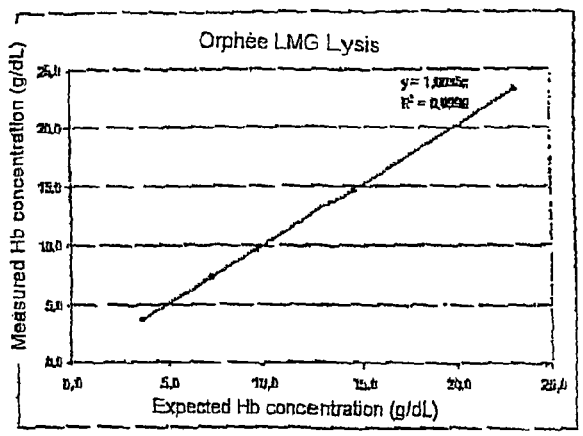
FIGS. 2a-2e are graphs of linearity tests of the measurement of haemoglobin by spectrophotometry according to the method of the invention.
Figure 2B:
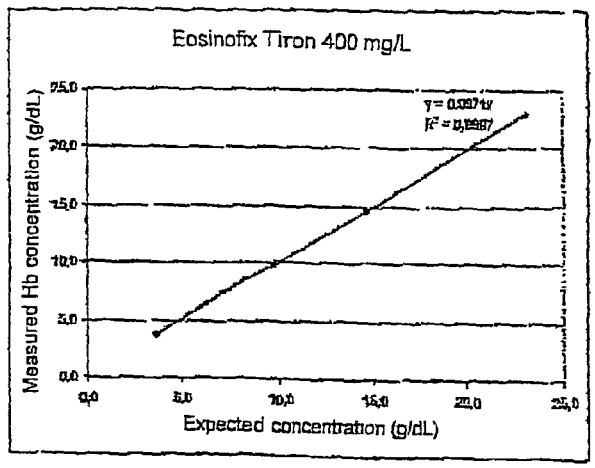
Figure 2C:
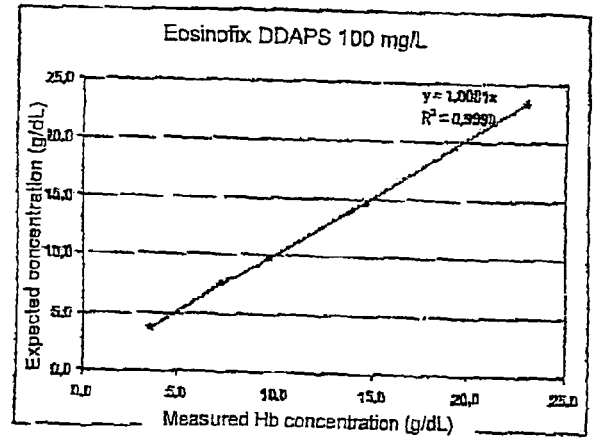
Figure 2D:
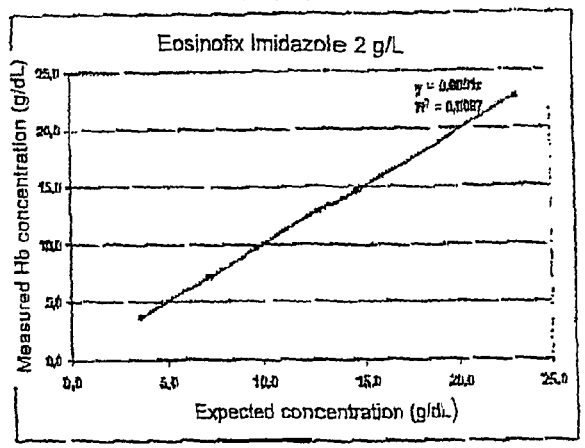
Figure 2E:
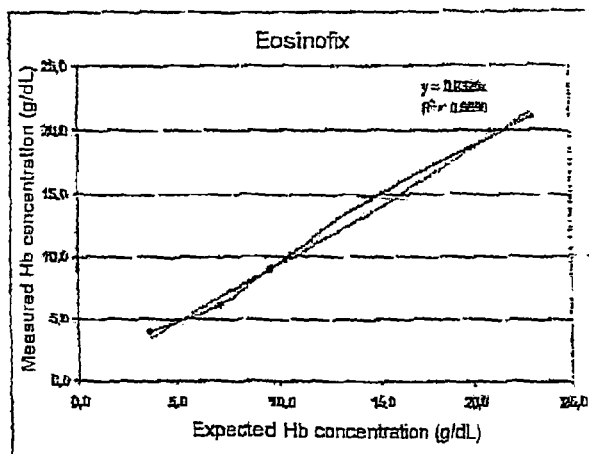
Figure 2F:
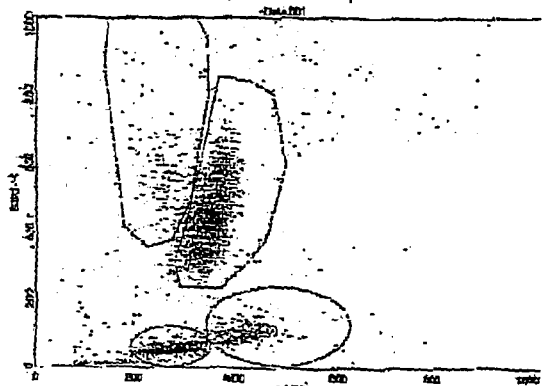
FIGS. 2f-2i are corresponding cytographs.
Figure 2G:
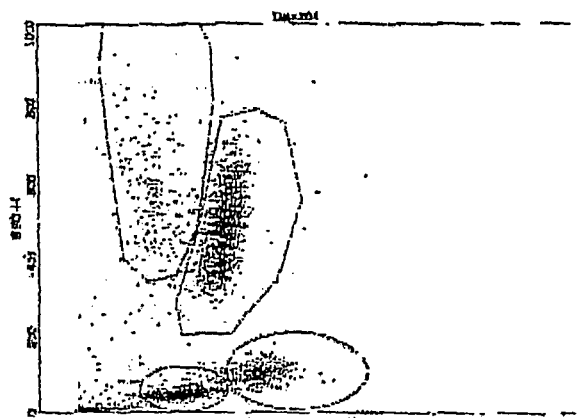
Figure 2H:
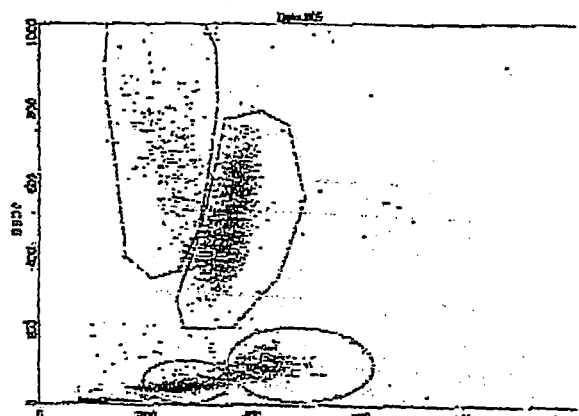
Figure 2I:
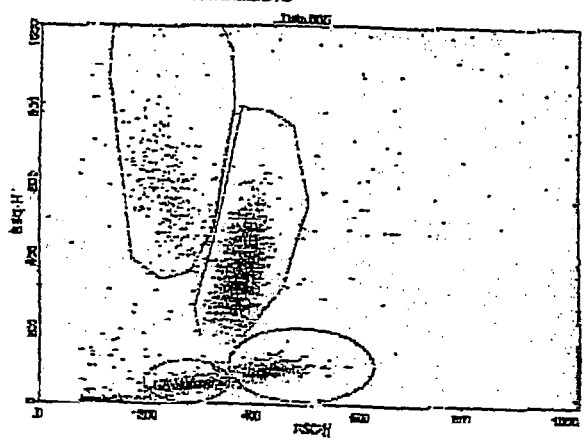

Measurement of the Haemoglobin by Spectrophotometry:

Linearity tests were carried out using a spectrophotometer at 542 nm. The graphs are shown in FIGS. 2a-2e. They represent the haemoglobin concentrations measured in relation to the expected concentrations. More specifically:

FIG. 2a corresponds to a reference lysis for measurement of the haemoglobin by spectrophotometry (LMG® sold by the company ORPHEE);

FIGS. 2b, 2c and 2d correspond to the mono-reagent according to embodiment No. 4 with, as stabilization agent of the haemoglobin complex, respectively Tiron, DDAPS and imidazole; and FIG. 2e corresponds to the method of the invention implemented using as mono-reagent Eosinofix® alone, i.e. containing no stabilization agent of the haemoglobin complex according to the present invention.

For the three tests carried out according to the invention, a positive linearity test is obtained for each with a correlation coefficient $R^2$ of $1\pm10^{-4}$ (shown in the figure). This result is in accordance with that obtained with the reference lysis of FIG. 2a. This means that the method of the invention does indeed allow measurement of a real haemoglobin level in a blood sample.

By contrast, as is seen in FIG. 2e, with the reagent (Eosinofix) without a hemoglobin stabilizer, a linear relationship is not obtained. This means that this reagent alone cannot be used to measure a haemoglobin level.

Leucocyte Differentiation by Flow Cytometry

FIGS. 2f to 2i are cytographs obtained using a BD FACScan® flow cytometer, corresponding respectively to Eosinofix alone and Eosinofix to which DDAPS, Tiron and imidazole are added. In these figures, it is seen that the differentiation of the sub-populations is indeed achieved and in a manner which is comparable to a standard reagent for leucocyte differentiation (matrix obtained with Eosinofix in FIG. 2f).

Reference can also be made to the cytograph of FIG. 11b (described below) in particular obtained with a cytometer according to the invention.

The hydraulic device according to the fourth object of the invention will now be described.

Figure 3:
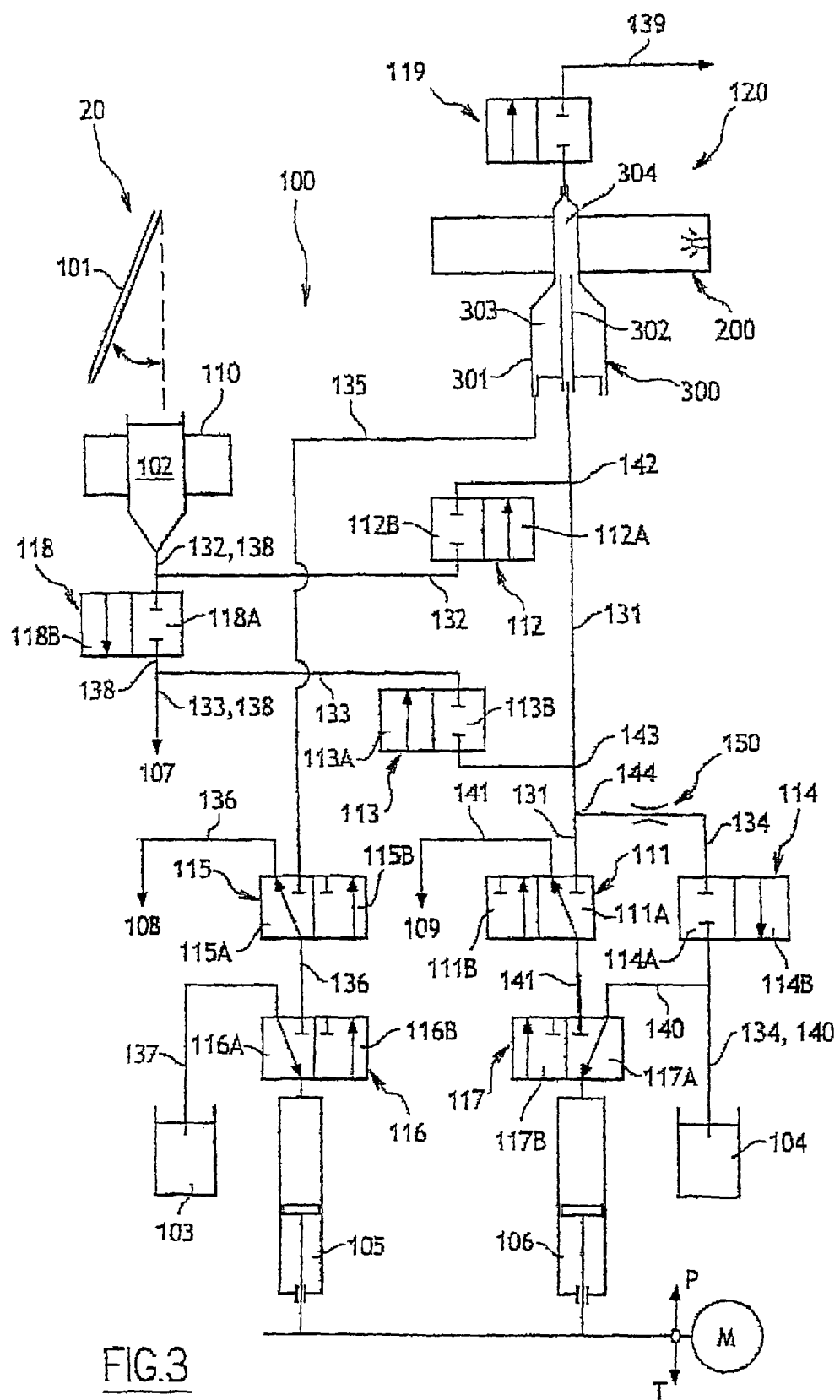
FIG. 3 is a diagrammatic view of an automatic apparatus for analysis of a blood sample using a hydraulic device according to the fourth object of the present invention.

FIG. 3 partially represents the diagram of a hydraulic system 100 and some of the equipment of an automatic blood analyzer 20, in so far as it allows an understanding of the hydraulic device according to the invention.

The automatic apparatus illustrated in FIG. 3 in particular comprises a needle 101 for sampling blood to be analyzed in a tube which was used for its storage and its transport to the automatic apparatus. The blood taken is poured by the needle in the form of a sample into a tank 102. The tank 102 is in particular designed for the dilution and/or the lysis of the erythrocytes of the blood sample. All or part of the sample, before or after dilution, can be taken with a view to analysis in another part of the automatic apparatus, for example in a device 120, described below. A device for analysis of the haemoglobin 110 (a spectrophotometer for example) is arranged close to the tank 102. A store 103 for a dilution product and a store 104 for a reagent, in particular a lysis reagent are connected to the tank 102 via the hydraulic circuit 100.

Another analysis device 120 is more specifically dedicated to the counting and differentiation of the leucocytes, for example on the whole or part of the sample taken from the tank 102. Hereafter sample will also refer to this whole or this part. The device for analysis of the leucocytes 120 in particular comprises an optical device 200 and an optical tank 300. The optical tank is connected to the tank 102 via the hydraulic circuit.

A set of syringes allows the movement of the liquids in the hydraulic circuit. Of these syringes, a syringe 105 dedicated to the diluent and a syringe 106 dedicated to the reagent are represented so that the invention is well understood. Other syringes which are not represented because they are not necessary in order to understand the invention can complete the device.

Besides the pipes for the circulation of the liquids, the hydraulic circuit comprises solenoid valves for the changeover of different circuits in the hydraulic circuit 100, according to its use at a given moment of the analysis. Eight solenoid valves 111-119 of the solenoid valves of the hydraulic circuit 100 are illustrated in FIG. 3. Each solenoid valve comprises two positions, each labelled respectively with the letter A or B.

The design of the hydraulic circuit as will be described below, allows the use of only one motorization M for the syringes illustrated. The same motorization can also be used for other syringes. Thus, the pistons of the syringes 105, 106 are firmly attached to each other. Their movement is therefore simultaneous, either pushing P, when they are driven into the respective cylinder of each syringe, or pulling T when they are withdrawn.

The arrangement and then the hydraulic operation of the automatic apparatus will now be described.

The tank 300 comprises an external body 301 and an injector 302, inside the body 301, a sleeving volume 303 is formed between the body and the injector.

The hydraulic circuit 100 comprises:

- an injection branch 131 which extends upstream of the injector, between the injector and the valve 111;
- a sample branch 132 which is connected at a sample branching point 142 to the injection branch and extends to the tank 102;
- a suction branch 133 which is connected at a suction branching point 143 to the injection branch, upstream of the sample branching point 142, via the valve 113 and extends to a vacuum source 107, for example a syringe or a peristaltic pump;
- a discharge branch 134 which is connected at a discharge branching point 144 to the injection branch, upstream of the suction branching point 143, and extends to the reagent product store 104;
- a sleeving branch 135 which extends upstream of the body 301 and connects the sleeving volume and the valve 115;
- a dilution branch 136 which extends between the valve 116 and a use 108 for the diluent via the valve 115;
- a diluent branch 137 which extends between the diluent store 103 and the valve 116;
- a reagent branch 140 which extends between the reagent store 104 and the valve 117;
- a reaction branch 141 which extends between the valve 117 and a use 109 for the reagent via the valve 111;
- a draining branch 138 for the tank 102 which extends between the tank 102 and the vacuum source 107 via the valve 118, the sample branch 132 being connected with the draining branch between the tank 102 and the valve 118, and the suction branch being connected to the outlet branch 132 beyond the valve 118 in relation to the tank; and,
- an outlet branch 139 which connects the downstream of the tank 300, via the valve 119, to a waste tank, for example at atmospheric pressure or via a suction source, a syringe or a peristaltic pump.

In a first position 116A of the valve 116, the dilution syringe 105 is in communication with the diluent store, so that a pulling movement T allows the syringe 105 to be filled with diluent.

In a first case the dilution syringe containing diluent, with the valve 116 being in its second position 116B which connects the syringe 105 to the dilution branch 136 and the valve 115 being in its first position 115A which connects the dilution branch to the use 108 for the diluent, a pushing movement P allows the diluent to be moved to this use 108, for example in the tank 102, for example for a dilution of the whole sample.

In a second case, with the valve 116 being in its second position 116B and the valve 115 being in its second position 115B which connects the dilution branch to the sleeving branch 135, a pushing movement P allows the diluent to be moved into the optical tank 300, in order to form a sleeving flow there. The usefulness of this sleeving flow in the context of the invention will be analyzed in a description of the tank 300 below.

The valve 117 being in a first position 117A which connects the syringe of reagent to the reagent store 104, and the valve 114 being in a first position 114A which shuts off the discharge branch 134, a pulling movement T allows the reagent syringe 106 to be filled with reagent.

In a first case, the reagent syringe containing reagent, with the valve 117 being in its second position 117B which connects the reagent syringe 104 to the reaction branch 141 and the valve 111 being in a first position 111A which connects the reaction branch to the use 109 for the reagent, a pushing movement P allows the reagent to be moved to this use 109, for example in the tank 102, for example for a lysis of the whole sample.

In a second case, the valve 117 being in its second position 117B and the valve 111 being in its second position 111B which connects the reaction branch 141 to the injection branch 131, the reagent syringe 106 is directly connected to the injector 302.

The valve 118 being in a first position 118A which isolates the suction branch 133 from the sample branch 132 through the draining branch, the valve 112 being in a first position 112A which connects the upstream part to the downstream part of the sample branch 132, the valve 113 being in a first position 113A which connects the downstream part to the upstream part of the suction branch 133, therefore to the vacuum source 107, the sample to be analyzed is sucked into the injection branch 131, between the sample branching point 142 and the suction branching point 143.

The discharge branch 134 comprises a variable or calibrated fluid resistance 150.

When the diluent syringe 105 contains diluent, the reagent syringe 106 contains reagent and a blood sample to be analyzed is in the injection branch 131; and when furthermore the valves 112, 113 are in their second positions 112B, 113B which isolate the upstream part and the downstream part from their respective arms; and when the valves 115, 116 are in their second positions 115B, 116B which connect the diluent syringe 105 to the sleeving volume 303; when finally the valves 111, 117 are in their second positions 111B, 117B which connect the reagent syringe 106 to the injector 302 and the valve 114 is in its second position 114B; a single pushing movement P generated by the single motorization M, allows the driving of the diluent, the reagent and the blood sample in the direction of and through the tank 300, while a part of the reagent, which is a function of the fluid resistance 150, is returned to the reagent store 104.

The resistance 150 in particular allows adjust of the flow rates of the sleeving and displacement liquids one with respect of the other. This allows these flow rates to be adapted to the different functions of these liquids. In particular, this allows similar flow velocities to be obtained for the sleeving and the sample in the analysis zone 304 when a standard hydrofocus tank is used.

In particular, the discharge branch 134 and the arrangements described previously make it possible to use a single motorization and therefore to reduce in particular the cost of an automatic analysis apparatus, as well as its bulk.

The diluent forms, in an analysis zone 304 of the tank 300 a sleeving flow for the sample (see in particular FIGS. 4 and 5). The reagent, situated upstream of the sample in the injection branch 131, serves as a displacement liquid, i.e. it allows the piston movement of the reagent syringe to be transmitted to the sample. Thus, there is no point in filling the reagent syringe with the sample in order to be able to undertake its analysis. Thus, even a sample of small volume can be analyzed, and all of this sample can be injected and analyzed without some of it remaining in the injection branch 131 or in the syringe 106.

Of course, other syringes, valves and branches, not represented in FIG. 3, can make up the hydraulic circuit 100, in order for the automatic analysis apparatus 20 to operate fully and well.

The optical device 200 according to the invention will now be described, in particular with regard to FIGS. 4 and 5.

The optical device comprises an approximately monochromatic light source 201. This light source is an electroluminescent diode. The light is principally emitted along an optical axis X200. The optical axis X200 is arranged approximately perpendicular to an injection axis X300 for movement of the sample in the optical tank 300. The two axes X200 and X300 together define an optical plane.

In order to prevent the source light beam 311 produced by the source 201 from being polluted by spurious light, a set of three diaphragms, is arranged, each one perpendicular, on the path of the beam. The diaphragms 202 are pierced with holes the diameter of which is approximately equal to the beam and is progressively increased in each diaphragm in order to adapt it to the diameter of the measurement beam as this diameter increases the further away from the source 201 it is. The beam then passes through a focusing device 203 constituted by one or more lenses.

Beyond the focusing device the beam encounters an adjustment device which allows the optical axis to be moved in a plane perpendicular to the injection axis X300, i.e. in a transverse direction in relation to the movement of the sample in the tank. A lateral shift of the beam can lead to a partial or no illumination of the sample which has a direct influence on the analysis result.

In the context of the example described, the adjustment device is constituted by a transparent slide 220 rotatably mounted about an axis X220. The axis 221 is approximately parallel to the injection axis X300. If the slide is arranged perpendicular to the optical axis X200, the beam passes through it without being deflected. By contrast, if the slide forms an angle with the optical axis, a double refraction, at entry and exit of the slide, shifts the beam in a plane perpendicular to the adjustment axis X220. The adjustment axis X220 being approximately parallel to the injection axis X300, only a transverse shift is generated by the refraction in the slide. The greater the thickness and/or the refractive index of the slide and the more the slide is inclined with respect to the optical axis the greater is the shift. Thus, for a slide with a chosen thickness and refractive index, it is sufficient to rotate the slide 220 about its axis X220 in order to adjust the position of the beam relative to the sample which moves in the analysis zone 304 of the optical tank 300. Such an adjustment device is particularly economical compared to the devices of the prior art, especially as a precise rotation is generally easier to carry out than a precise translation, using high-precision mechanics.

After having penetrated the tank and passed through the sample, the source beam 211 at least partially becomes an axially-resulting beam 212, which exits the tank approximately along the optical axis. The axially-resulting beam 212 carries information about the sample which it has passed through.

In order to allow simultaneous measurements of several of these items of information it must be possible to analyze the beam with several measurement apparatuses 222, 223. In particular, the optical analysis relies on the detection of the light diffracted according to two ranges of angles: narrow angles and wide angles. In each of the ranges of angles, two different items of information are used. It is therefore necessary to distribute the light in two different channels for each range. Therefore means 205 for separating the resulting beam 212 into two resulting beams 213, 214 are used. The separation means are mainly constituted by a beam splitter 205. This beam splitter is a transparent glass slide. It is arranged at 45 degrees to the optical axis. A secondary axially-resultant beam 213, formed by the light which has passed through the beam splitter, and a beam resulting from loss 214 formed by the Fresnel losses, i.e. by the light reflected by the beam splitter, are thus produced.

Such a beam splitter has a very low cost compared to the separation means used in the prior art in optical analysis devices of this type. In particular, because it does not comprise any additional reflective coating, it is virtually age resistant and requires practically no maintenance. Given the multiple reflections inside the slide and the polarization of the incident radiation of the axially-resulting beam, between 5 and 15% of the energy is reflected, the rest being transmitted in the form of the secondary axially-resulting beam.

Between the tank and the beam splitter, the axially-resulting beam 212 is rendered parallel by suitable means 206. Beyond the beam splitter, the resulting beams 213, 214 are again focussed by respective suitable means 207, 208, with a view to their analysis by the respective measurement apparatuses 222, 223.

In the example described, the measurement apparatus 222, which analyzes the secondary axially-resulting beam 213 is an apparatus for measurement of the diffraction close to the optical axis by the blood cells (called an FSC measurement). In the example described, the measurement apparatus 223, which analyzes the beam produced by the Fresnel losses 214 is an apparatus for measurement of the light losses in the axis (called an ALL measurement), i.e. the obscuring of the light by the cells in the sample.

FIG. 5 diagrammatically represents a section of the tank in a plane perpendicular to the injection axis X300 and containing the optical axis X200. As is particularly illustrated in this figure, the light reemitted laterally by the sample in a laterally-resulting flow 315, focussed beyond the tank in a measurement apparatus 224, is also analyzed.

An optical tank according to the invention, in particular envisaged for use with a hydraulic circuit such as described previously, will now be described, in particular with reference to FIG. 6. The operation of this tank can be compared with a hydrofocus-type operation of the prior art, which is represented very diagrammatically in FIG. 10.

The tank 350 of FIG. 10 comprises a body 351, an injector 302 and an analysis zone 354. An internal transverse dimension D354 of the tank is approximately 250 microns. This dimension can be a diameter, if the tank has a circular section, or one side, if it has a square or rectangular section. As illustrated by the dotted lines, a sleeving flow 362 is used to reduce in particular the diameter of a sample flow 361, so that in the analysis zone 354 the sample flow has, in the prior art, a diameter D361 of less than 50 microns.

Figure 6:
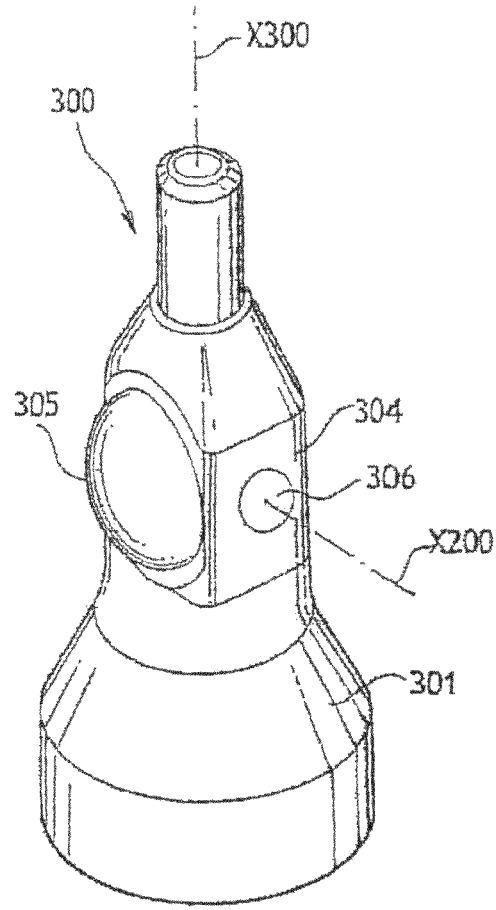
FIG. 6 is a perspective view of an optical tank according to the third object of the invention.

The tank 300 according to the invention, illustrated in FIGS. 4-6, comprises the body 301 and the injector 302, arranged approximately coaxially along an injection axis X300. The analysis zone 304 is arranged downstream of the injector.

The body is produced from an injected material, preferably from a plastic material. Such a production method allows complex shapes to be obtained. In particular, a lens 305 is moulded in the body. This lens allows the light which is obscured, diffracted or diffused by the blood cells to be collected.

This lens must have dimensions, in particular sufficient diameter for the possible local inhomogeneities in the injected material to be negligible in relation to these dimensions. In the example illustrated, the lens 305 has a diameter of about 3 mm. This injected lens is a lateral lens 305 which the laterally-resulting beam 315 passes through. Moreover, the lateral lens must allow the light to be collected in as many directions as possible, i.e. with a directional field which is as large as possible. Thus, the closer the lens is to the sample, the greater the directional field. In the example illustrated, the lens is a hemispherical lens, called a 90° lens. Moreover, the lens being a part of the wall of the tank, there is direct contact with the liquid in the tank, i.e. there is no air space, with a low refractive index, between the sample and the lens. This improves the measurement.

In order to overcome the homogeneity deficiencies, glass is used where the light is particularly focussed, for example a glass of the BK7 type. This is the case in particular for the axial windows 306, where the source beam 211 penetrates the tank and where the axially-resulting beam 212 exits it.

In order to be able to produce an injected lens with such dimensions, it is necessary, in the analysis zone, for the tank 300 to have at least comparable dimensions. Moreover these large dimensions allow glass windows to be integrated into plastic walls, while the tanks of the prior art, having small dimensions, are made with walls entirely of glass or quartz. In the example illustrated in particular in FIGS. 5 and 6, the lower section of the tank is 4.5 mm along the optical axis by 3 mm in the perpendicular direction. This rectangular section with large dimensions associated with a small volume of the sample, which transports the blood cells to be analyzed, requires the use of a hydrodynamic sleeving of the sample. By way of comparison, a tank of the prior art has an internal transverse dimension D354 of the analysis zone close to 250 microns.

Upstream of the analysis zone 304, the body 301 of the tank surrounds the injector 302 and forms around the injector the sleeving volume 303. The walls of the injector separate a flow 311 formed by the sample, inside the injector, from a sleeving flow 312, in the sleeving volume. The sample flow originates from the injection branch 131 of the hydraulic circuit 100. The sleeving flow originates from the sleeving branch 135 of the hydraulic circuit. In the analysis zone, the two flows are in contact, remain concentric and flow simultaneously in the tank.

In order to reduce the production costs of the automatic apparatus, it can be advantageous to reduce the precision of the production of the parts. As mentioned above, such an aim can be achieved by creating a sample flow with a larger section.

However, if a technique of the prior art is used where the sample flow is stretched by a sleeving flow, a sample flow with a large section will be turbulent, which in particular adversely effects the precision of measurements. Moreover the section of the sample flow will be progressively reduced, which is the opposite of the effect desired, which is to have a sample flow with a large section. Such an aim is achieved by using the hydraulic circuit 100 according to the invention, described previously with reference to FIG. 1. Such a circuit makes it possible to obtain independently chosen velocities for the flow of the sleeving flow and for that of the sample flow, in order that little turbulence appears in the sample flow and that this turbulence has no notable effect on the analysis result. The two flows can each be approximately uniform, optionally laminar in certain appropriate velocity ranges.

Figure 7:
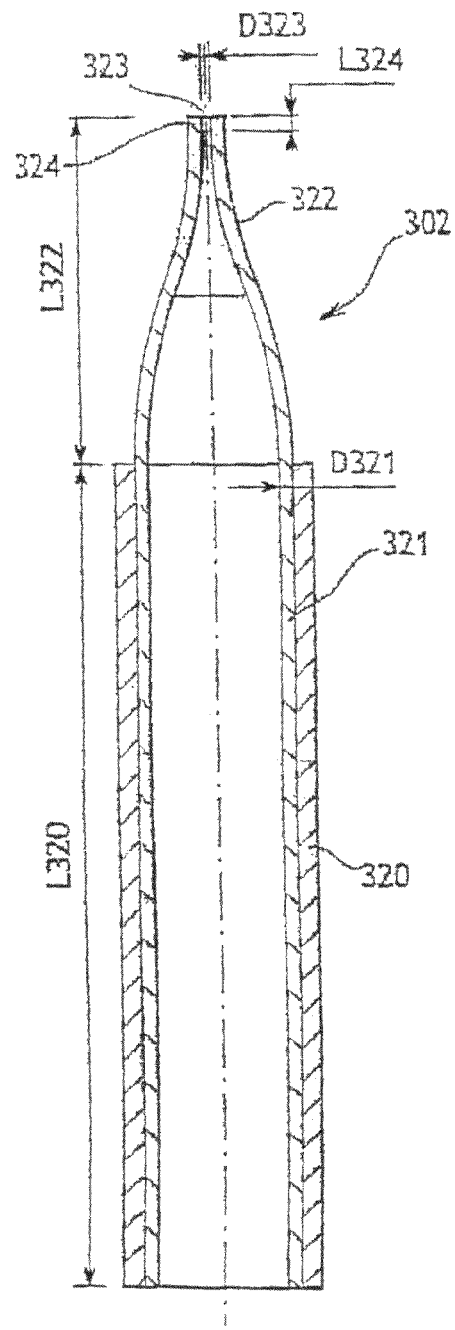
FIG. 7 is a longitudinal section view of a first embodiment of an injector for an optical tank according to the invention.

Moreover, an injector 302 as illustrated in FIG. 7 or FIG. 8 also allows limitation of the turbulence in the sample flow. Moreover, it allows a high velocity of injection of the sample into the optical tank, while retaining its flow approximately uniform.

An injector 302 as illustrated in FIG. 7 comprises a structural tube 320, for example made of stainless steel ensuring the stiffness of the injector. The structural tube is sheathed on the inside with a tube 321 made of a plastic, for example a polytetrafluoroethylene (PTFE). In the example illustrated the structural and sheathing tubes are cylindrical. The sheathing tube is extended, downstream of the structural tube, by a nozzle made of the same plastic material. The fact of differentiating the structural function of the structural tube and the injection function of the nozzle, associated with the use of a plastic material, allows sufficiently precise shapes to be obtained at a low cost.

The nozzle has a section which is progressively narrowed from an internal diameter D321 of the sheathing tube to an internal diameter D323 of an outlet orifice 323 at a downstream end 324 of the nozzle 322. In the example described, the downstream end 324 is a cylinder with a length L324. The wall of the nozzle is initially inwardly concave, then inflected to become inwardly convex, the section of the nozzle thus being progressively narrowed from the upstream to the downstream, from the diameter D321 to the diameter D324. The concave surface is tangent to the inner surface of the cylindrical sheathing tube. The convex surface is tangent to the inner surface of the cylindrical end 324. In the example described, the diameter D323 of the orifice 323 is approximately 60 microns, the internal diameter D321 of the sheathing tube is approximately 1 millimetre, the length L322 of the nozzle is approximately 2.5 millimetres, that L320 of the structural tube is approximately 6 millimetres and that of the cylindrical end L324 approximately 200 microns.

An injector 302 such as that illustrated in FIGS. 8 and 9 is in a single piece and made of a single substantially stiff material. This material can be, for example, stainless steel, a ceramic, a synthetic ruby or a plastic material. The plastic material can advantageously be a polytetrafluoroethylene. The injector comprises an approximately cylindrical tube 331 which is extended downstream by a nozzle 332.

The nozzle progressively narrows inwardly, from an internal diameter D331 for the tube 331, to an internal diameter D333 of an outlet orifice 333 for the sample, at a downstream end 334 of the nozzle 332. In the example illustrated, the narrowing takes place according to a truncated cone open at an angle preferably comprised between 9 and 10 degrees. Beyond the truncated cone and up to the outlet orifice 333, the diameter remains constant in a cylindrical part 335, with a length L335 and a diameter D333.

On the exterior of the nozzle, its external diameter is progressively larger according to a truncated cone open at an angle comprised between approximately 8 and 9 degrees, then, in the noticeably more reduced end according to a truncated cone open at an angle A334 comprised between approximately 35 and 45 degrees, to an external diameter D334 around the outlet orifice 333. D334 is approximately 3 to 4 times larger than D333.

By way of example D333=60 μm, D334=200 μm and A334=40°.

Thanks to the different arrangements described previously, it is possible to obtain a high injection velocity. Thus, in the example described it is possible to inject a sample of more than 200 microlitres in less than 10 seconds. In particular, such an injection rate makes it possible to use a high rate of dilution of the blood sample, without increasing the duration of the analysis compared to automatic apparatuses of the prior art. In particular, the same dilution, for example $1/160^{th}$, can be used for the analysis of the haemoglobin by the device 110 (see FIG. 3) and for the analysis of the leucocytes by the optical device 120, instead of $1/80^{th}$ generally used for the analysis of the leucocytes.

Figure 11A:
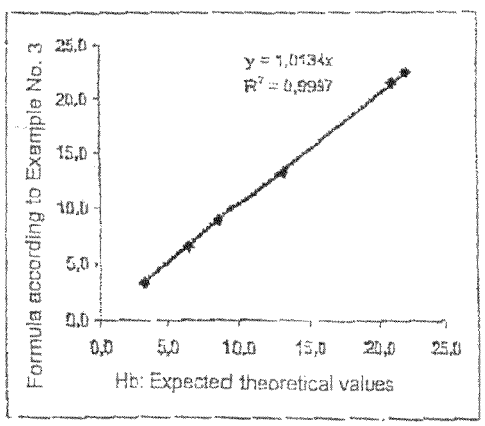
FIGS. 11a-11c are graphs illustrating results obtained with an automatic apparatus using the method of the invention and using a cytograph with the optical device and tank according to the invention.
Figure 11B:
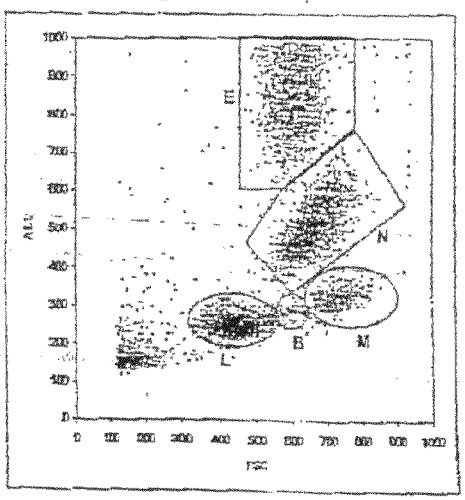
Figure 11C:
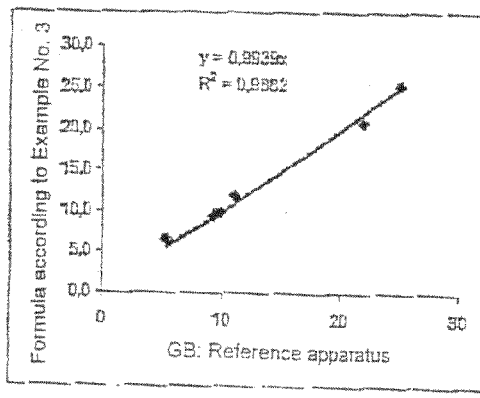

FIGS. 11a-c illustrate the results obtained using the method and the equipment according to the first object of the invention, said equipment using an optical tank 7 according to the third object of the invention and an optical device 8 according to the second object of the invention. FIG. 11a shows a positive linearity test of the haemoglobin measurement and therefore demonstrates the possible and reliable measurement of the haemoglobin level of a blood sample according to the invention. FIG. 11b shows an optical matrix obtained from a test sample of blood with 30% eosinophils to which the formulation according to the invention has been added. On this matrix, the five sub-populations are present and differentiated (groups delimited in the cytograph: E for eosinophils, N for neutrophils, M for monocytes, B for basophils and L for lymphocytes). FIG. 11c shows the positive linearity test of the measurement by resistivity of the level of leucocytes.

These figures show that thanks to the invention it is possible to carry out an analysis of at least the level of haemoglobin and the level of leucocytes and a leucocyte differentiation using the formulation according to the invention, in particular in the form of a mono-reagent.

Of course, the invention is not limited to the examples which have just been described and numerous modifications can be applied to these examples without exceeding the scope of the invention.

For example, products other than the diluent or the reagent can be used in order to form respectively the sleeving flow and the fluid piston, particularly if they are available in the automatic apparatus for other uses.

In addition, instead of being arranged only on the injection circuit, a fluid resistance can be arranged on the sleeving circuit or on both of these simultaneously. This can occur as a function of the given maximum flow rate via the means for displacement of the liquids intended respectively for displacement or sleeving.

Several or all of the lenses of the optical tank and/or of the optical device can thus be produced by injection with the body of the tank, instead of a single one as illustrated previously. In particular, the glass windows can be injected. Particularly if the inhomogeneities in the injected material are more or less negligible with regard to the precision desired for the measurements.

An adjustment device and/or the separation means described previously can be used independently of each other and optionally with a light source other than an electroluminescent diode.

The invention claimed is:

1. A flow-through tank (300) for an optical device (120) for counting and/or differentiation of leucocytes in an automatic blood analysis apparatus (20), comprising:
    a tank body (301);
    an injector (302) arranged approximately coaxially with the tank body (301) along an injection axis (X300) for injecting a sample flow (311);
    an analysis zone (304) connected to the tank body and arranged downstream from the injector (302) having a section with at least one transverse dimension between 1 and 5 millimeters; and
    means (301) for forming a sleeving flow around the sample flow, said sample flow being injected under pressure relative to the sleeving flow, the sleeving flow being passive in that the sleeving flow does not stretch the sample flow.

2. The tank according to claim 1, wherein at least the body of the tank is formed of an injected material.

3. The tank according to claim 2, further comprising:
    at least one lens (305) moulded in one piece with the tank body.

4. The tank according to claim 3, wherein the at least one lens comprises a lens provided to be arranged laterally with respect to an optical axis.

5. The tank according to claim 4, wherein the at least one lens comprises a hemispherical lens.

6. The tank according to claim 3, further comprising:
    at least two windows (306) on the analysis zone of the tank along an optical axis penetrating the analysis zone, a first of the two windows for entry of a light beam and a second of the two windows for the beam to exit.

7. The tank according to claim 6, wherein the tank and at least one of the two windows are moulded in a single piece with the analysis zone.

8. The tank according to claim 6, wherein at least one window (306) is an insert made of a transparent material.

9. The tank according to claim 1, wherein the injector comprises an outlet orifice (323, 333), the outlet orifice having a diameter between 20 microns and 150 microns.

10. The tank according to claim 1, wherein the injector is produced in a single piece from a more or less rigid material.

11. The tank according to claim 10, wherein the injector is made of ceramic.

12. The tank according to claim 10, wherein the injector is made of synthetic ruby.

13. The tank according to claim 10, wherein the injector is made of stainless steel or a plastic material.

14. The tank according to claim 1, wherein the injector comprises a rigid structural tube (320) and, inside the structural tube, a sheathing tube (321) made of a plastic material extended by a nozzle (322) and formed in a single piece with the sheathing tube.

15. The tank according to claim 14, wherein the plastic material of the injector is a polytetrafluoroethylene.

16. A haematology apparatus (20), comprising:
    a tank (300), comprised of a tank body (301), an injector (302) arranged approximately coaxially with the tank body (301) along an injection axis (X300) for injecting a sample flow (311), an analysis zone (304) connected to the tank body and arranged downstream from the injector (302) having a section with at least one transverse dimension between 1 and 5 millimeters, and means (301) for forming a sleeving flow around the sample flow, said sample flow being injected under pressure relative to the sleeving flow,
    wherein the sleeving flow is passive in that the sleeving flow does not stretch the sample flow.

17. The tank according to claim 7, wherein at least one window (306) is an insert made of a transparent material.

18. The tank according to claim 9, wherein the injector is formed as a single piece from a more or less rigid material.

19. The tank according to claim 9, wherein the injector comprises a rigid structural tube (320) and, inside the structural tube, a sheathing tube (321) made of a plastic material extended by a nozzle (322) and formed in a single piece with the sheathing tube.

* * * * *